(12) United States Patent
Jennings

(10) Patent No.: US 7,030,631 B1
(45) Date of Patent: Apr. 18, 2006

(54) METHOD AND APPARATUS FOR MONITORING AND DETERMINING THE MOISTURE CONTENT OF A SUBSTANCE IN A CONTAINER

(76) Inventor: Thomas A. Jennings, 112A Bala Ave., Bala Cynwyd, PA (US) 19004

( * ) Notice: Subject to any disclaimer, the term of this patent is extended or adjusted under 35 U.S.C. 154(b) by 0 days.

(21) Appl. No.: 10/905,019

(22) Filed: Dec. 10, 2004

(51) Int. Cl.
*G01R 27/26* (2006.01)

(52) U.S. Cl. ...................... 324/689; 324/665

(58) Field of Classification Search ............... None
See application file for complete search history.

(56) References Cited

U.S. PATENT DOCUMENTS

| | | | |
|---|---|---|---|
| 4,282,480 A * | 8/1981 | Fujito et al. ............. 324/665 |
| 4,549,134 A | 10/1985 | Weiss | |
| 5,445,178 A | 8/1995 | Feuer | |
| 5,898,309 A | 4/1999 | Becker et al. | |
| 6,114,863 A | 9/2000 | Krahn et al. | |
| 6,348,809 B1 | 2/2002 | Hirota et al. | |
| 6,462,562 B1 * | 10/2002 | Svoboda et al. ............ 324/663 |
| 6,756,793 B1 | 6/2004 | Hirono et al. | |

* cited by examiner

*Primary Examiner*—Vincent Q. Nguyen
(74) *Attorney, Agent, or Firm*—Malin, Haley & DeMaggio, P.A.

(57) ABSTRACT

A method and apparatus for monitoring and determining the moisture content of a sample substance inside a closed container. The apparatus includes a parallel capacitance circuit formed by a source of AC voltage supplied to a reference container and a sample container. The method does not require penetration or opening of the sealed sample container nor the destruction of the sample, and can be used to rapidly determine moisture content under normal storage conditions or at elevated or lower temperatures that may be used in a drying process.

7 Claims, 1 Drawing Sheet

METHOD AND APPARATUS FOR MONITORING AND DETERMINING THE MOISTURE CONTENT OF A SUBSTANCE IN A CONTAINER

FIELD OF THE INVENTION

This invention relates generally to an apparatus and method for monitoring and determining the moisture content of a substance in a container and, specifically, to an apparatus or method for monitoring and determining the moisture content of a substance in a container without direct sample use or destruction of the sample.

DESCRIPTION OF RELATED ART

The amount of moisture in a substance is one of the most important factors in determining the useful life of a material. A wide variety of materials used as foods or healthcare products are dried to extend the length of time for which they can be stored. While in most cases excessive moisture shortens the storage time, or shelf life, of a product, there are some substances containing proteins for which the stability, and therefore, the storage time, is actually reduced by over-drying or the removal of too much water. Thus, when producing such substances, the moisture content must be controlled within certain defined limits to achieve the desired stability and storage time. This can be accomplished by controlling the humidity and temperature of the container holding the substance during the drying process. Once an acceptable moisture content has been attained, this value must be maintained during storage. Therefore, a means of measuring the moisture content, both during the drying process and during subsequent storage, is imperative to ensuring the quality of the substance.

Current methods for determining the moisture content of a substance during the drying process and while in storage include measuring the loss in weight of a given mass of a substance after the drying process is completed, as well as the Karl Fischer method in which a sample of the subject substance is dissolved in methanol or other suitable solvent and then by measuring the quantity of hydrogen iodide that forms in the presence of water still remaining in the sample of the substance. Both of these methods require that a portion of the sample substance be removed for destructive testing during the drying process. Until now, there have been no known non-destructive, non-invasive methods for determining the moisture content of a substance during a drying process. Numerous shortcomings are inherent in both of these testing methods. The methods destroy the samples used so that they are unavailable for use or repeat testing. Moisture content cannot be tracked under high humidity and high temperature conditions. Additionally, the Karl Fischer method can only be used to test the moisture content of substances that are soluble in methanol or other suitable solvent, which excludes proteins from being tested with this method (proteins are not soluble in methanol). Pooling of the samples also results in false high or false low moisture content values depending on the difference between the relative humidity of the samples and the environment.

U.S. Pat. No. 4,549,134, issued to Weiss on Oct. 22, 1985, describes a method and device for measuring the moisture content of various fluids. The device comprises a membrane immersed directly in the fluid for which the moisture content is to be measured. The '134 invention may operate in either D.C. or A.C. mode, and in the A.C. mode a pair of capacitor plates are pressed in contact with each side of the membrane to measure changes in capacitance of the fluid, thereby allowing a determination of the moisture content of the subject fluid. This invention has several drawbacks, namely that the device must be inserted directly into the liquid so that the container must be opened, and also the technique described by the '134 invention is effective for measuring the moisture content of fluids but not of substances in other phases, such as solids.

U.S. Pat. No. 6,114,863, issued to Krahn et al., on Sep. 5, 2000, describes a method for determining the presence of water in a material in which a set of electrodes are placed on the surface of a layer of the material being monitored with an electric field established between said electrodes. The phase angle for the electric field is measured at a predetermined frequency and is compared with a predetermined phase angle for a dry portion of the same material. A difference between the predetermined and the measured phase angles indicates the presence of water in the subject material. The '863 invention is most useful for determining the moisture content of insulating material surrounding an electrical generator. This invention requires that the electrodes be in direct contact with the material for which the presence of water is to be determined. The '863 invention is also not useful for determining the moisture content of a substance in a closed container.

In U.S. Pat. No. 6,756,793, issued to Hirono et al., on Jun. 29, 2004, a capacitance type moisture sensor and method for constructing said sensor is described. This invention includes a sensor housing that has an electrically-insulating wall with a pair of electrodes disposed on its surface and a circuit unit including a capacitance-detecting circuit. One of the electrodes is positioned on the inner surface of the electrically-insulating wall while the outer surface of said wall faces a space in which the moisture content is to be measured. The electric field between the two electrodes forms the moisture-detecting region of the capacitance-detecting circuit. An output circuit produces an electrical signal that corresponds to the amounts of water based upon the capacitance value determined by the capacitance-detecting circuit. The '793 invention is particularly well-adapted for measuring the moisture content of garbage contained in a garbage vessel. This invention requires placement inside the container holding the material for which the moisture content is to be measured, and thus, is not effective for determining the moisture content of a substance within a closed container that is either in storage or undergoing a drying process.

U.S. Pat. No. 6,348,809, issued to Hirota et al., on Feb. 19, 2002, describes a microscopic capacitance measurement system that includes a prober, a signal line, and a capacitance measurement circuit. The prober comprises a box into which the sample substance to be tested is placed. A detection terminal within said prober box must be placed in contact with the sample for which the capacitance is to be measured. Therefore, this invention is also ineffective for determining the moisture content of a substance within a closed container because the detection terminal of the signal line must be in direct contact with the sample substance.

Similarly, U.S. Pat. No. 5,898,309, issued to Becker et al., on Apr. 27, 1999, describes an apparatus and method for determining specific material characteristics of plastics, such as impedance, where the plastic material is placed between the electrodes of a capacitive sensor located inside a container. Again, this invention is not effective for determining the moisture content of a substance inside a closed container without opening said container, and moreover, is directed toward the measurement of the impedance of plastics rather than to determining moisture content of a substance.

Finally, U.S. Pat. No. 5,445,178, issued to Feuer on Aug. 29, 1995, describes a soil moisture sensor comprising a pair of elongated conductive sensor elements coupled as part of an LC oscillator circuit. In this invention, the probe-like sensor elements must be buried or pushed into the ground to obtain accurate readings of soil moisture content. As with the previously discussed patents found in the prior art, the '178 invention cannot be used to determine the moisture content of a sample substance in a closed container without the need to penetrate said container in some way and for some period of time.

SUMMARY OF THE INVENTION

This invention relates to an apparatus and method for determining the moisture content of a substance in a container, comprising a sample container, a reference container, a desiccant, a capacitance meter that provides a known frequency of AC voltage, a plurality of electrical contacts used to supply the AC voltage from said capacitance meter simultaneously to said sample and said reference containers, an inverting circuit, and a resistor in the output of said sample container. A parallel capacitance circuit is created by the connection of said sample container and a reference container to a source of AC voltage using wires and electrical contacts.

The percentage of moisture in a substance stored in a container is related to the number of monolayers of moisture on the interior surface of the container at a given temperature and is independent of the dimensions of said container or the mass of the substance. The reference container may have no adsorbed moisture on the interior surface or may contain a known number of adsorbed monolayers of moisture. Thus, the reference container must contain either a desiccant, or a known quantity of water sealed therein, which can be substituted in place of the desiccant.

The inverting circuit amplifies the output of the reference container by a factor of 1 and changes the sign of the output signal. The resistor in the output of said sample container ensures that the time constants of the output of the sample container circuit and the reference container circuit match.

By creating the parallel capacitance circuit using the reference container and the sample container, which contains the sample substance, such as a food, electrical, or pharmaceutical product, the changing moisture content of said sample substance can be monitored during the drying process by measuring the effect of changes in the number of monolayers of adsorbed moisture on the interior surface of a sample container on the dielectric properties of said container. This measurement is accomplished by determining the difference in electrical properties of a dielectric sample container, such as the capacitance, capacitive reactance, and/or the quality factor, with respect to the reference container. (The drying process is defined in terms of a difference in electrical properties of the dielectric containers.) The number of monolayers of moisture adsorbed on the interior surface of a container is related to the amount of residual moisture in a substance contained in the container. A change in the number of monolayers of moisture adsorbed on the interior surface of a container is related, under given operating conditions, to the temperature of the substance.

A significant number of samples of a substance can be examined and monitored during the drying process, thereby allowing the determination of the completion of a given segment of the drying process with a higher degree of confidence than has previously been possible using current conventional methods, such as temperature probes which can contaminate the product or a pressure rise test. The relative amount of residual moisture in a substance can be determined based on a sample that does not require pooling from various containers in a batch to obtain a sufficient amount of substance as can be required when using a conventional method to determine the moisture content. Using this method, all of the substance produced can be inspected for moisture content without destruction of the sample.

Another advantage of this invention is that a change in the moisture content of a substance in a sample container can be determined under normal storage conditions or at elevated or lower temperatures. During storage, the invention can be used to determine the residual moisture content of a substance within a storage container. The moisture content of a substance in storage is determined by measuring the number of monolayers of adsorbed moisture on the interior surface of a sample container on the dielectric properties of said container. As with monitoring the moisture content of a substance undergoing a drying process, the number of monolayers of moisture adsorbed on the interior surface of a container in storage is related to the amount of residual moisture in a substance contained in the container.

An object of this invention is to provide an apparatus and method for monitoring determining the moisture content in a sample container containing a pharmaceutical or other sample substance or systems without requiring penetration or opening of the closed container.

Another object of this invention is to provide a faster and more economical method for repetitive determinations of the moisture content of a sample substance within a container that is either in storage or to monitor the moisture content of a substance undergoing a drying process.

Yet another object of this invention is to provide a method for determining the moisture content within a container containing a pharmaceutical or other sample substance and/or system without destroying said sample or system.

Still another object of this invention is to provide a method and apparatus that permits determining the moisture content of a sealed container under both elevated and lower temperatures.

An additional object of this invention is to provide a method for determining the moisture content of a substance that does not require that the sample substance be soluble in methanol.

In accordance with these and other objects which will become apparent hereinafter, the instant invention will now be described with particular reference to the accompanying drawings.

DETAILED DESCRIPTION

Figure 1:
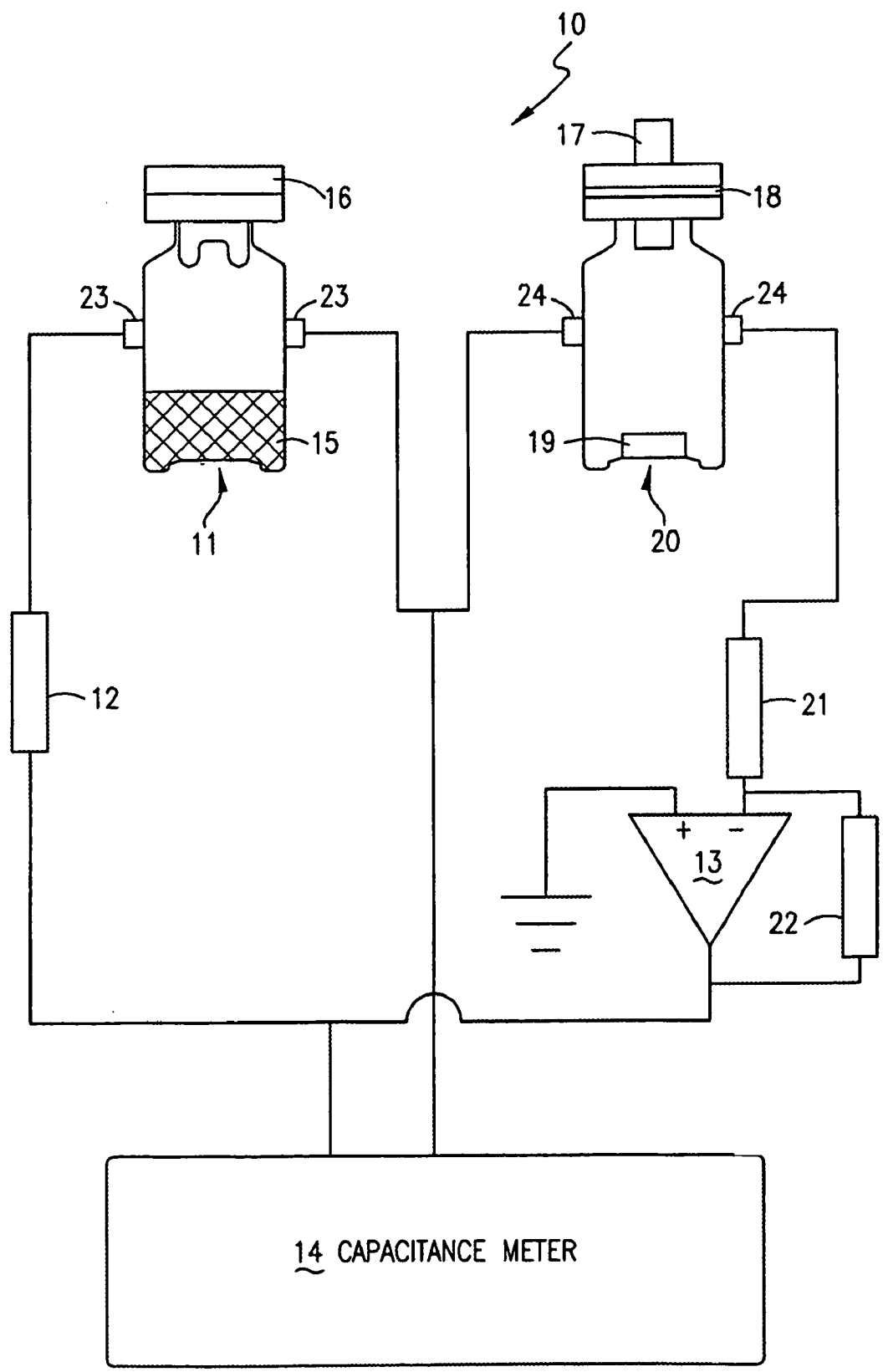
FIG. 1 shows a schematic diagram of the invention and its parallel capacitance circuit.

FIG. 1 illustrates the invention 10 for monitoring and determining the moisture content of a substance in a container, comprising a sample container 11 containing a substance 15 for which the moisture content is to be determined, a reference container 20, a capacitance meter 14 that provides a known frequency of AC voltage, a plurality of electrical contacts 23 and 24 used to apply the AC voltage from said capacitance meter 14 simultaneously to said sample container 11 and said reference container 20, an inverting circuit, and a source of resistance 12 in the output of said sample container. Both the sample and reference containers are constructed from a dielectric material such as glass and certain plastics. Preferably, said reference container 20 will have no adsorbed moisture on the interior surface. A desiccant 19, and preferably the desiccant $P_4O_{10}$, will be placed into the reference container 20 to ensure that all adsorbed moisture is removed from the interior surface. However, a known quantity of liquid water or water vapor may be sealed within said reference container in place of the desiccant. The apparatus can record accurate measurements when a known number of adsorbed monolayers of moisture are present in the reference container 20.

A plurality of wires connects the capacitance meter 14 to the electrical contacts 23 and 24 which are attached to the exterior surface of the sample container 11 and reference container 20. This arrangement creates a parallel capacitance circuit. Each electrical contact has a known area and may be constructed from any known electrical conductor, including stainless steel. The wires connecting said electrical contacts 23 and 24 to form the circuit may also be constructed from any known electrical conductor. The sign inverting circuit comprises an operational amplifier 13 and two resistors 21 and 22. The inverting circuit amplifies the output of the reference container 20 by a factor (gain) of 1 and changes the sign of the input signal.

A resistor 12 connected in series with the parallel capacitance circuit of the apparatus receives capacitance output from the sample container 11. The resistance provided by this resistor 12 in the output of the sample container 11 matches the time constant of the output of the reference container 20 with the output of the sample container 11 to ensure that the time constants of the two outputs are equal.

The invention 10 provides a novel and convenient method to accurately and quickly determine the moisture content within a sample container 11 containing substance such as a pharmaceutical substance 15. The invention will also be useful for measuring the moisture content of containers holding foods, cosmetics, electrical devices, and other substances with which moisture content or infiltration into a storage container might be of particular concern.

Once the sample substance 15 is placed into the sample container 11, said sample container is sealed with a standard elastomer closure 16. The reference container 20 is sealed with a special glass plate 17 that is fused to form a glass seal 18 over the opening of said reference container. The special glass seal 18 is not a part of this invention and will be known to those skilled in the art. A known quantity of water or, more preferably, a desiccant 19, is placed into the reference container 20. The present invention also has the benefit that measurements taken using this method do not require penetration or opening of the container, pooling of samples from several containers to acquire a sample great enough for the moisture content to be measured, nor the destruction of any of the sample substance during the measuring process.

Moisture adsorbed on the inside surface of said sample container 11 is produced by humidity generated by the desorption of water from the surface of the substance 15 in said sample container 11. The residual moisture of a substance is chemically related to the relative humidity and temperature as well as the amount of water adsorbed on the surface of the material in the container. For example, the amount of moisture adsorbed on the surface of the material in the container is inversely related to the temperature, such that a decrease in temperature of the container would be accompanied by a corresponding increase in the amount of water adsorbed to the surface of the container. Therefore, the number of adsorbed monolayers of water, at a given temperature, is directly related to the amount of residual moisture adsorbed on the surface of the substance. As the ratio of the partial pressure of water to the vapor pressure at a given temperature equals or falls below 0.70, only one monolayer or less of water will adsorb to the surface of the container. However, when this ratio exceeds 0.70, the number of monolayers of adsorbed moisture may increase many-fold.

The moisture content of the sample and reference containers can be determined by measuring and comparing the capacitance of the moisture layer adsorbed to the interior surfaces of said containers. This measurement accepts that the thickness of each container are similar and that the gases in the container will have a negligible effect on electrical measurements. For example, the capacitance of the adsorbed moisture layer is determined by the equation:

$$C_a = C_n - C_o,$$

where $C_o$ represents the capacitance of a container in the absence of any adsorbed moisture or where a known quantity of water is adsorbed to the container surface, $C_n$ represents the capacitance of the container with "n" (n>0) adsorbed layers of water, and $C_a$ represents the capacitance of the adsorbed moisture layer. The difference in capacitance obtained using the equation above is used to determine the presence of water adsorbed on the interior surface of the container.

The presence of a layer of water adsorbed on the inside surface of a container may result in an increase in the quality factor (Q), which is defined as an inverse function of the energy that is dissipated by the capacitor. Q can be expressed as:

$$Q = C \times V,$$

where V is the voltage applied by the capacitance meter 14. When a layer of adsorbed water is present, $Q_o < Q_n$, where $Q_o$ is the quality factor for the container's surface in the absence of moisture and $Q_n$ is the quality factor in the presence of "n" layers of water. Therefore, a difference in $Q_n$ may also be used to determine the number of monolayers of water adsorbed to the surface of a container.

Because the electrical contacts 23 are attached to the exterior surface of the sample container 11, said contacts 23 can be positioned so as to monitor several sample containers in a batch undergoing a drying process. In this way, a frequency distribution is established to allow the operator to ascertain the probability that a given sample container has not completed a particular step of the drying process or the probability that a substance in a sealed container has moisture values outside of the defined limits for that particular substance.

The method and apparatus can also be used to determine the moisture content of products under storage to ascertain whether moisture is entering the storage container under normal storage conditions. This method could be beneficial to test for either a random failure or a general failure of a particular storage container.

The instant invention has been shown and described herein in what is considered to be the most practical and preferred embodiment. It is recognized, however, that departures may be made therefrom within the scope of the invention and that obvious modifications will occur to a person skilled in the art.

What is claimed is:

1. An apparatus for monitoring and determining the moisture content of a substance, comprising:
   a closed sample container having an interior surface and an exterior surface;
   a reference container having an interior surface and an exterior surface;
   a desiccant placed in said reference container to eliminate moisture;
   a capacitance meter that provides a known frequency of AC voltage;
   a plurality of electrical contacts connected to the exterior surface of said sample container, the exterior surface of said reference container, and to said capacitance meter to apply the AC voltage from said capacitance meter simultaneously to said sample and said reference containers, each electrical contact having a known surface area;
   an output circuit connected to said electrical contacts mounted to said sample container;
   an inverting circuit connected to said capacitance meter and said output circuit; and
   a source of electrical resistance in said output circuit of said sample container, whereby electrical differences between the sample container and the reference container are used to determine the moisture content of a sample in the closed sample container without opening the sample container.

2. The invention according to claim 1, wherein the connection of said sample container and a reference container to a source of AC voltage forms a parallel capacitance circuit.

3. The invention according to claim 1, wherein said inverting circuit amplifies the output of the reference container by a factor of 1 and changes the sign of the output signal.

4. The invention according to claim 1, wherein said resistance in the output of said sample container matches the time constant of the output of the reference container circuit.

5. The invention according to claim 1, wherein said reference container does not contain any adsorbed moisture on the interior surface or contains a given amount of adsorbed moisture on the interior surface.

6. The invention according to claim 1, wherein the desiccant, preferably $P_4O_{10}$, is sealed inside said reference container.

7. The invention according to claim 1, wherein a known quantity of water, sealed within said reference container, is substituted in place of the desiccant.

* * * * *